(12) United States Patent
Nagar et al.

(10) Patent No.: US 12,683,032 B2
(45) Date of Patent: Jul. 14, 2026

(54) DIGITAL TWIN COMPUTER SIMULATION USING SYNCHRONIZATION OF BODY ORGAN FOR DETERMINING COMPATIBILITY

(71) Applicant: International Business Machines Corporation, Armonk, NY (US)

(72) Inventors: Raghuveer Prasad Nagar, Kota (IN); Sarbajit K. Rakshit, Kolkata (IN); Amitava Kundu, Bangalore (IN); Sidharth Ullal, Chennai (IN)

(73) Assignee: International Business Machines Corporation, Armonk, NY (US)

( * ) Notice: Subject to any disclaimer, the term of this patent is extended or adjusted under 35 U.S.C. 154(b) by 656 days.

(21) Appl. No.: 17/660,322

(22) Filed: Apr. 22, 2022

(65) Prior Publication Data

US 2023/0343465 A1 Oct. 26, 2023

(51) Int. Cl.
*G16H 50/50* (2018.01)
*G16H 50/20* (2018.01)

(52) U.S. Cl.
CPC ............. *G16H 50/50* (2018.01); *G16H 50/20* (2018.01)

(58) Field of Classification Search
CPC ........ G16H 20/40; G16H 40/63; G16H 40/67; G16H 50/20; G16H 50/50
See application file for complete search history.

(56) References Cited

U.S. PATENT DOCUMENTS

2013/0177972 A1 7/2013 Green
2018/0168464 A1* 6/2018 Barnett, Jr. ........ A61B 5/02055
2021/0229362 A1* 7/2021 Kofidis ................. G06T 7/0012

OTHER PUBLICATIONS

"3D Bioprinting of Living Tissues", Harvard University, Wyss Institute, last printed Apr. 6, 2022, 6 pages, <https://wyss.harvard.edu/technology/3d-bioprinting/>.
"3D Bioprinting: Eradicating Transplantation Waiting Lists And Testing Drugs On Living Tissues", The Medical Futurist, Mar. 11, 2021, 10 pages, <https://medicalfuturist.com/3d-bioprinting-overview/>.
"Biomodex", Dassault Systemes, 3DExerperience Lab project, last printed Apr. 6, 2022, 7 pages, <https://3dexperiencelab.3ds.com/en/projects/life/biomodex/>.
"Digital Surgery Deploys First Surgical Artificial Intelligence System for the Operating Room", Business Wire, Jul. 16, 2018, 3 pages, <https://www.businesswire.com/news/home/20180716005146/en/Digital-Surgery-Deploys-Surgical-Artificial-Intelligence-System>.
Albright, Brian, "Low-Cost Human Organ Printing", Digital Engineering, Nov. 16, 2015, 2 pages, <https://www.digitalengineering247.com/article/low-cost-human-organ-printing/>.

(Continued)

*Primary Examiner* — Mark D Remaly
(74) *Attorney, Agent, or Firm* — Michael A. Petrocelli

(57) ABSTRACT

Generating, using a computer, a digital twin model or simulation for organ transplant or organ repairs where organ data of an organ for a patient is received at a computer. Organ parts are identified based on organ data, and the organ parts include a retained portion of the organ and a replacement portion of the organ. A digital model is generated as a digital twin simulations of the organ parts based on the received organ data. Parameters for the organ parts is determined, which include dimensions of the retained portion of the organ and dimensions of the replacement portion of the organ.

12 Claims, 10 Drawing Sheets

(56)         References Cited

OTHER PUBLICATIONS

An, et al., "Application of Machine Learning in 3D Bioprinting: Focus on Development of Big Data and Digital Twin", International Journal of Bioprinting, vol. 7, No. 1, Article 342, Jan. 2021, 6 pages, <https://www.researchgate.net/publication/348906140>.

Anonymous, "Method and system for digital twin-based realtime and predicted health condition visualization with augmented reality glass", An IP.com Prior Art Database Technical Disclosure, IP.com No. IPCOM000262365D, IP.com Electronic Publication Date: May 23, 2020, IP., 5 pages, <https://priorart.ip.com/IPCOM/000262365>.

Chowdhury, Hasan, "Liver success holds promise of 3D organ printing", Financial Times, Mar. 5, 2018, 5 pages, <https://www.ft.com/content/67e3ab88-f56f-11e7-a4c9-bbdefa4f210b>.

Griffin, Matthew, "Soldiers digital twins let US Army 3D print replacement body parts in battle", Fanatical Futurist, Jan. 5, 2017, 3 pages, <https://www.fanaticalfuturist.com/2017/01/digital-clones-will-let-US-army-3d-print-new-body-parts-in-battle-to-treat-injured-soldiers/>.

Kilic, et al., "Organs-on-chip monitoring: sensors and other strategies", Microphysiological Systems, vol. 2, No. 5, Sep. 2018, 32 pages, <https://mps.amegroups.com/article/view/4689/5479>.

Little, et al., "Printing the future: 3D bioprinters and their uses", Australian Academy of Science, last printed Apr. 6, 2022, 14 pages, <https://www.science.org.au/curious/people-medicine/bioprinting>.

Marchal, Thierry, "Will Digital Twins Improve Healthcare for Their Real-World Counterparts?", ANSYS, Blog, Aug. 7, 2018, 3 pages, <https://www.ansys.com/en-in/blog/will-digital-twins-improve-healthcare-real-world-counterparts>.

Mell, et al., "The NIST Definition of Cloud Computing", National Institute of Standards and Technology, Special Publication 800-145, Sep. 2011, 7 pages.

Mevea, "How can Digital Twin technology improve your business?—Digital Twin explained", YouTube, Oct. 11, 2018, 1 page, <https://www.youtube.com/watch?v=fEl5oz33la8>.

Sargent, Kara, "What is Digital Twins (+Impact on Business Modernization)", Learn Hub, Jan. 18, 2018, 9 pages, <https://learn.g2.com/trends/digital-twins>.

Van Houten, Henk, "How a virtual heart could save your real one", Philips, Nov. 12, 2018, 11 pages, <https://www.philips.com/a-w/about/news/archive/blogs/innovation-matters/20181112-how-a-virtual-heart-could-save-your-real-one.html>.

* cited by examiner

100

Gathering data, using a digital twin computing system, from sensors regarding the health status of a patient and an organ for replacement or repair.
104

Identifying one or more organs of the person.
108

Assigning a unique number, using the computing system, to the identified organs.
112

Identifying an organ portion or portions of an organ, and assigning a unique number to each portion of one or more organs.
116

Gathering data including video or photos from one or more IoT feeds from a physical patient, in real time, or near real time, using the digital twin computing system.
120

Synchronizing a digital model with its physical twin counterpart to maintain an updated digital physical twin.
124

Maintaining digital twin models with defined vital parameters of each of a plurality of an organ.
128

Storing digital models or digital twin models in a digital storage environment.
132

Updating received data which includes determining, for example, latest current condition of a patient, latest medications or medication updates, etc.
136

Identifying which portion of the organ is having a problem and will need to be replaced.
140

Identifying which portion of the organ needs to be replaced, and will be creating a digital twin model of the organ portion needing to be transplanted.
144

To Block 148

FIG. 1A

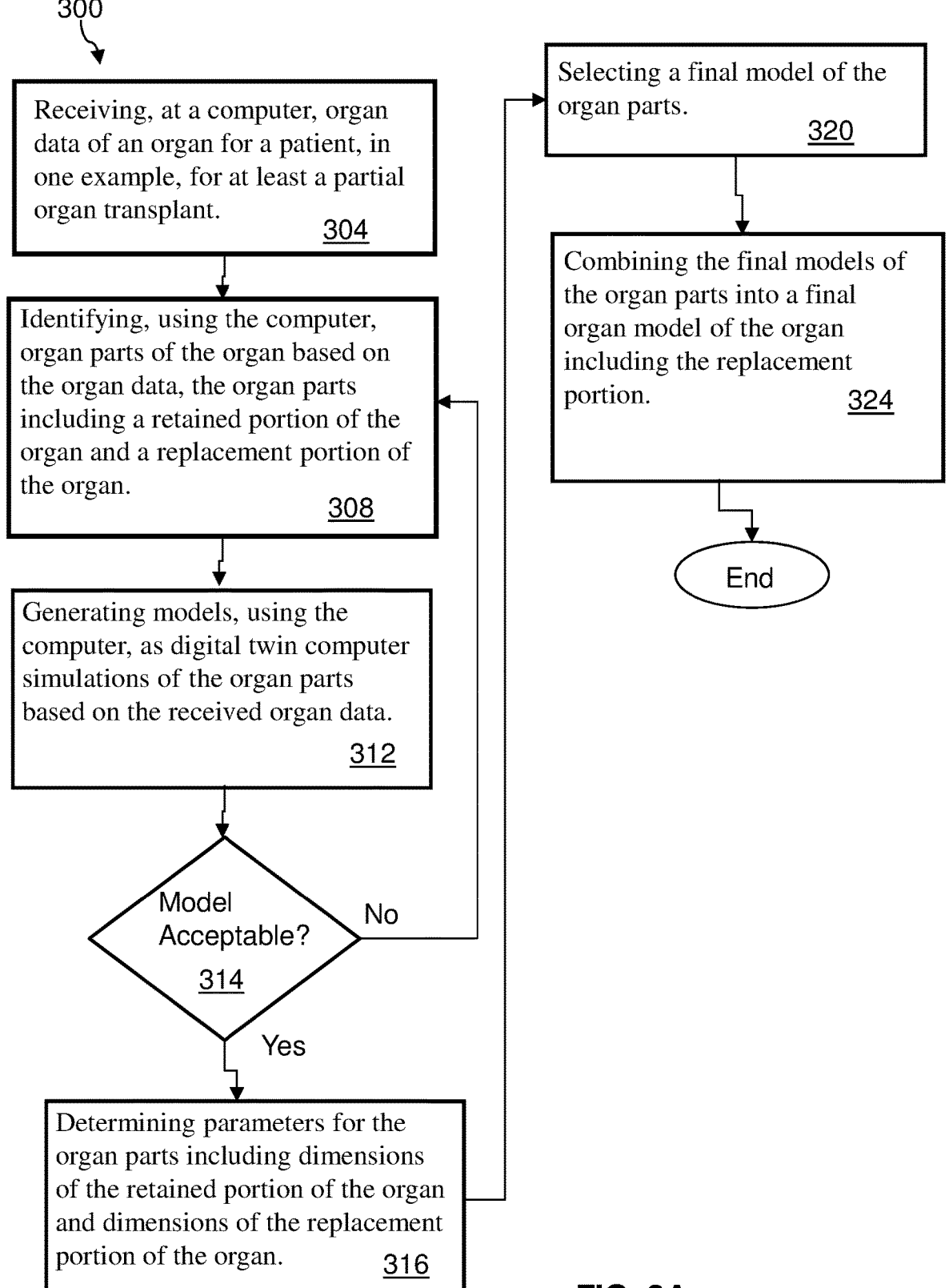

300

Receiving, at a computer, organ data of an organ for a patient, in one example, for at least a partial organ transplant.          304

Identifying, using the computer, organ parts of the organ based on the organ data, the organ parts including a retained portion of the organ and a replacement portion of the organ.          308

Generating models, using the computer, as digital twin computer simulations of the organ parts based on the received organ data.          312

Model Acceptable?          314

No

Yes

Determining parameters for the organ parts including dimensions of the retained portion of the organ and dimensions of the replacement portion of the organ.          316

Selecting a final model of the organ parts.          320

Combining the final models of the organ parts into a final organ model of the organ including the replacement portion.          324

End

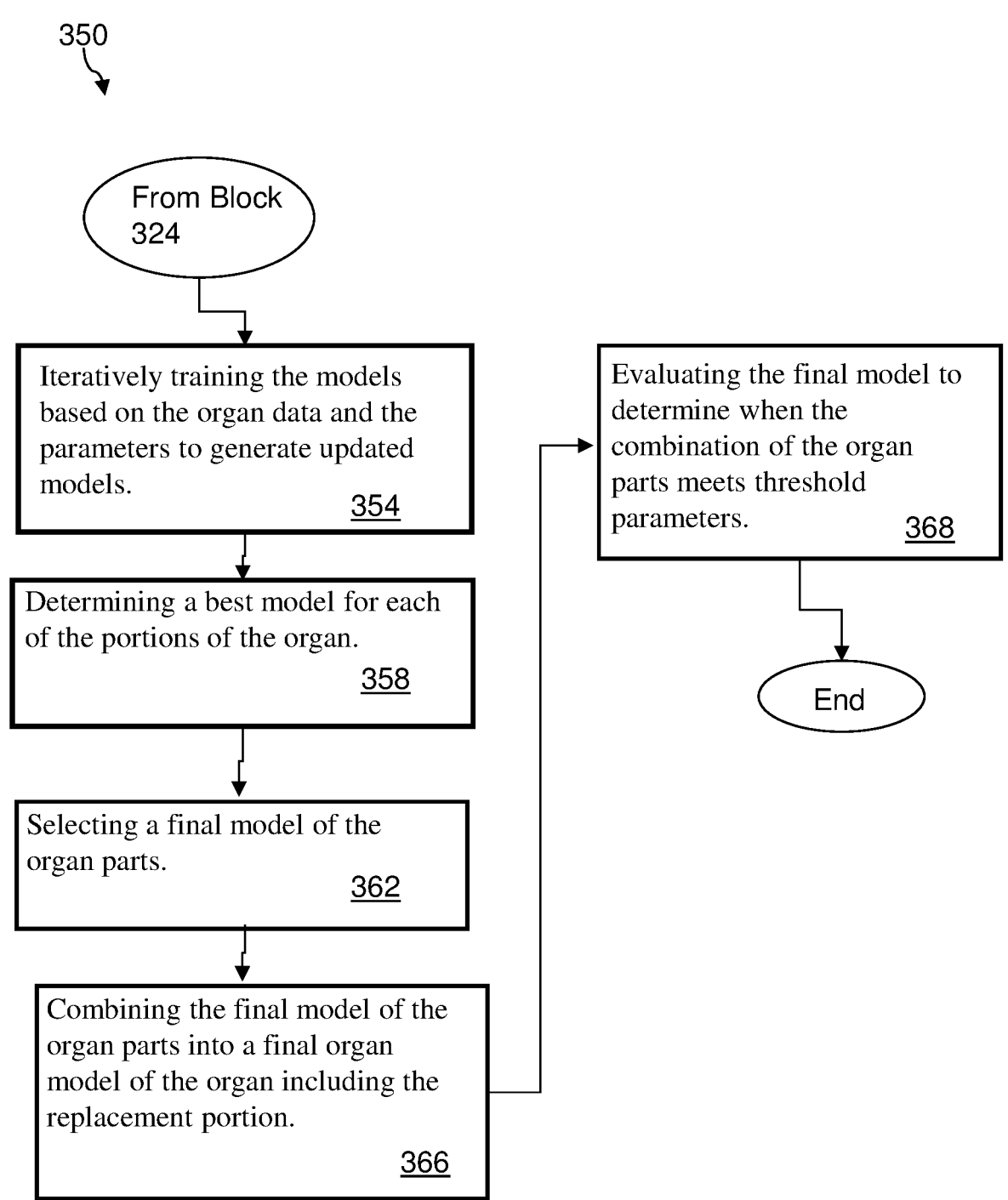

From Block
324

Iteratively training the models based on the organ data and the parameters to generate updated models.                                                354

Determining a best model for each of the portions of the organ.                                                358

Selecting a final model of the organ parts.                                                362

Combining the final model of the organ parts into a final organ model of the organ including the replacement portion.                                                366

Evaluating the final model to determine when the combination of the organ parts meets threshold parameters.                                                368

End

DIGITAL TWIN COMPUTER SIMULATION USING SYNCHRONIZATION OF BODY ORGAN FOR DETERMINING COMPATIBILITY

BACKGROUND

The present disclosure relates to determining, using digital twin computer simulation, body organ parts compatibility of body organ parts in a transplant medical procedure.

A bioprinting process can take cells from donor organs and use the cells to generate a printable bioink. A bioink can be a material used to produce engineered (artificial) live tissue using 3D printing technology, where the bioink can use cells and additional carrier materials. For example, layers of cells can be laid down in carefully calculated designs to build up small sections of liver tissue.

In another example, body parts, e.g., human body parts can be printed with a 3D (3 dimensional) bioprinting method. Using bioprinting, body parts can be printed, e.g., bone, skin, blood vessels, or internal organs, etc. For example, printing human tissue using 3D printing can include using cells from a person and culturing so that the cells multiply. Cultured cells can be loaded into a specialized bioprinter. The cells can be layered using hydrogel as a support. The cells can be grown into a mature tissue which are ready for use in a medical procedure.

SUMMARY

The present disclosure recognizes the shortcomings and problems associated with current techniques for bioprinting a portion of a body part or a partial organ, which should include identifying how much or a portion of the organ or body part is to be printed, so that the printed parts is compatible with the remaining organ. Embodiments of the present disclosure can reduce various complications. More particularly, embodiments of the present disclosure can include determining compatibility and synchronization of a generated organ part with a retained organ part.

For example, based on the condition of heart of a patient, proper flexibility and strength should be considered while printing valve of the heart, otherwise the heart and the valve may not be able to perform the activity in s synchronized manner, and gradually, there can be complications. What is needed is a technique by which system can validate how the bioprinting will be synchronized with remaining parts of the organ, in order to offer automatic and accurate bioprinting.

A digital twin is an exact digital replica of a product, process or service. This living model creates a thread between the physical and digital world. Internet of things (IoT) can connect objects using digital replication, enabling simulations, testing, modeling and monitoring based on the data collected by IoT sensors. Like everything in the realm of IoT, data is the primary driver, and most invaluable output, of digital twins. The sharing and analysis of digital twin data empowers companies to make decisions which directly impact their key performance indicators.

According to embodiments of the present disclosure, a system and method can include digital twin computing system for creating an exact working model of the body or organ parts and can validate how the working model will be synchronized with remaining parts of the organ. Accordingly, an appropriate digital twin model of a body or organ parts can be created so that bioprinting is productive and efficient.

Using a digital twin approach for bioprinting an organ, to print a complete or partial organ can be used. For example, for a complete organ printing, such as a heart printing, can include a printing of a valve of a heart.

In an aspect according to the present invention, a computer-implemented method for generating a digital twin model or computer simulation of an organ for organ transplant or organ repairs. The method includes receiving, at a computer, organ data of an organ for a patient. The method includes identifying, using the computer, organ parts of the organ based on the organ data, the organ parts including a retained portion of the organ and a replacement portion of the organ. The method includes generating models, using the computer, as digital twin computer simulations of the organ parts based on the received organ data; and determining parameters for the organ parts, the parameters including dimensions of the retained portion of the organ and dimensions of the replacement portion of the organ.

In a related aspect, the method includes selecting a final model for each of the organ parts; and combining the final models of the organ parts into a final organ model of the organ including the replacement portion.

In a related aspect, the method further includes iteratively training the models based on the organ data and the parameters to generate updated models; and determining a best model for each of the portions of the organ.

In a related aspect, the method further includes iteratively training the models based on the organ data and the parameters to generate updated models; determining a best model for each of the portions of the organ; selecting a final model of the organ parts; combining the final model of the organ parts into a final organ model of the organ including the replacement portion; and evaluating the final model to determine when the combination of the organ parts meets threshold parameters.

In a related aspect, the method further includes receiving data, at the computer, from devices and sensors connected to the patient.

In a related aspect, the method further including receiving data, at the computer, from Internet of Things (IoT) devices with respect to the patient, and receiving data from sensors connected to the patient.

In a related aspect, the method further including assigning, using the computer, a unique number to the model, wherein the unique number is a barcode.

In a related aspect, the retained part of the organ is a healthy portion of the organ and the replacement part of the organ is an unhealthy portion of the organ.

In a related aspect, the method further includes receiving data, at the computer, from Internet of Things (IoT) devices with respect to the patient, and receiving data from sensors connected to the patient; and updating the models based on the received data from the IoT devices and the sensors to generate a near real time simulation using the updated models.

In a related aspect, the method further including identifying, using the computer, the unhealthy portion of the organ using the updated models and other medical data received by the computer, wherein the other medical data includes medical diagnostic information and medical standards related to the organ.

In a related aspect, the method further including determining a part of the organ for replacement based on the identification of the unhealthy portion of the organ.

In a related aspect, the method further including printing, using a 3-dimensional bioprinting system, an organ part based on the model.

In another aspect according to the present invention, a system for generating a digital twin model or computer simulation of an organ for organ transplant or organ repairs includes a computer system. The computer system includes a computer processor, a computer-readable storage medium, and program instructions stored on the computer-readable storage medium being executable by the processor, to cause the computer system to perform the following functions to; receive, at a computer, organ data of an organ for a patient; identify, using the computer, organ parts of the organ based on the organ data, the organ parts including a retained portion of the organ and a replacement portion of the organ; generate models, using the computer, as digital twin computer simulations of the organ parts based on the received organ data; and determine parameters for the organ parts, the parameters including dimensions of the retained portion of the organ and dimensions of the replacement portion of the organ.

In a related aspect, the method further including causing the computer system to select a final model for each of the organ parts; and combine the final models of the organ parts into a final organ model of the organ including the replacement portion.

In a related aspect, the system includes causing the computer to iteratively train the models based on the organ data and the parameters to generate updated models; and determine a best model for each of the portions of the organ.

In a related aspect, the system further includes: iteratively train the models based on the organ data and the parameters to generate updated models; determine a best model for each of the portions of the organ; select a final model of the organ parts; combine the final model of the organ parts into a final organ model of the organ including the replacement portion; and evaluate the final model to determine when the combination of the organ parts meets threshold parameters.

In a related aspect, the system further includes causing the computer system to receive data, at the computer, from devices and sensors connected to the patient.

In a related aspect, the system further causes the computer system to receive data, at the computer, from Internet of Things (IoT) devices with respect to the patient, and receiving data from sensors connected to the patient.

In a related aspect, the system includes causing the computer system to assign, using the computer, a unique number to the model, wherein the unique number is a barcode.

In another aspect according to the present invention, a computer program product for generating a digital twin model or computer simulation of an organ for organ transplant or organ repairs, the computer program product comprising a computer readable storage medium having program instructions embodied therewith, the program instructions executable by a computer to cause the computer to perform functions, by the computer, comprising the functions to; receive, at a computer, organ data of an organ for a patient; identify, using the computer, organ parts of the organ based on the organ data, the organ parts including a retained portion of the organ and a replacement portion of the organ; generate models, using the computer, as digital twin computer simulations of the organ parts based on the received organ data; and determine parameters for the organ parts, the parameters including dimensions of the retained portion of the organ and dimensions of the replacement portion of the organ.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. The drawings are discussed forthwith below.

FIG. 1A is a flow chart illustrating a method, implemented using the system shown in FIGS. herein, for generating a digital twin model or computer simulation of an organ for organ transplant or organ repairs, which can include an artificial intelligence (AI) model and data analysis, according to an embodiment of the present disclosure.

FIG. 3A is a flow chart illustrating another method, implemented using the system shown in FIG. 4, for generating a digital twin model or computer simulation of an organ for organ transplant or organ repairs, which can include an artificial intelligence (AI) model and data analysis, according to an embodiment of the present disclosure.

FIG. 3B is a flow chart illustrating another method, implemented using the system shown in FIG. 4 and continuing from the method 300 shown in FIG. 3A, for generating a digital twin model or computer simulation of an organ for organ transplant or organ repairs, which can include an artificial intelligence (AI) model and data analysis, according to an embodiment of the present disclosure.

DETAILED DESCRIPTION

The following description with reference to the accompanying drawings is provided to assist in a comprehensive understanding of exemplary embodiments of the invention as defined by the claims and their equivalents. The description includes various specific details to assist in that understanding, but these are to be regarded as merely exemplary, and assist in providing clarity and conciseness. Accordingly, those of ordinary skill in the art will recognize that various changes and modifications of the embodiments described herein can be made without departing from the scope and spirit of the invention. In addition, descriptions of well-known functions and constructions may be omitted.

The terms and words used in the following description and claims are not limited to the bibliographical meanings, but are merely used to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Embodiments and Examples

Embodiments and figures of the present disclosure may have the same or similar components as other embodiments. Such figures and descriptions of illustrate and explain further examples and embodiments according to the present disclosure.

Figure 1B:
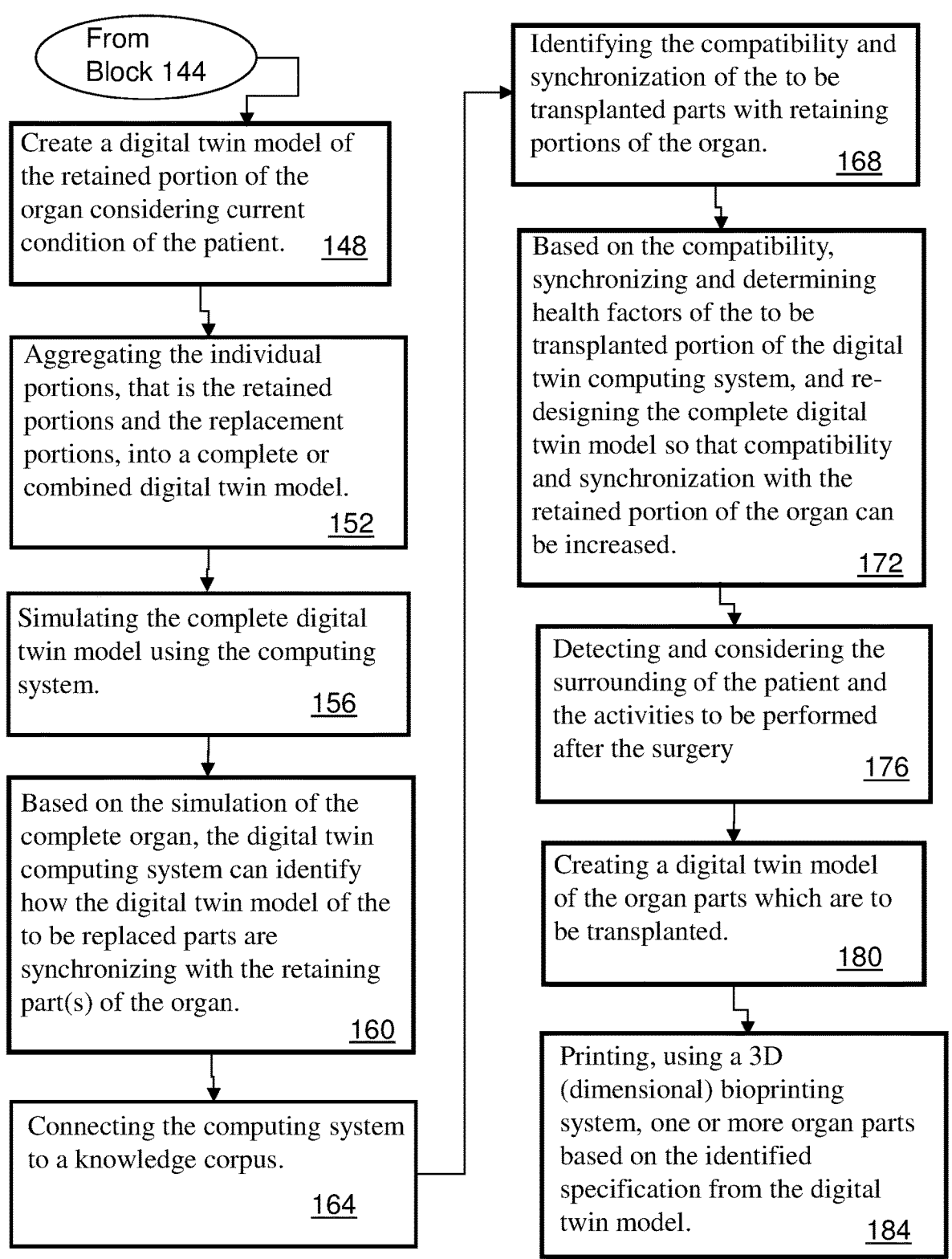
FIG. 1B is a flow chart illustrating a continuation of the method shown in FIG. 1.
Figure 2:
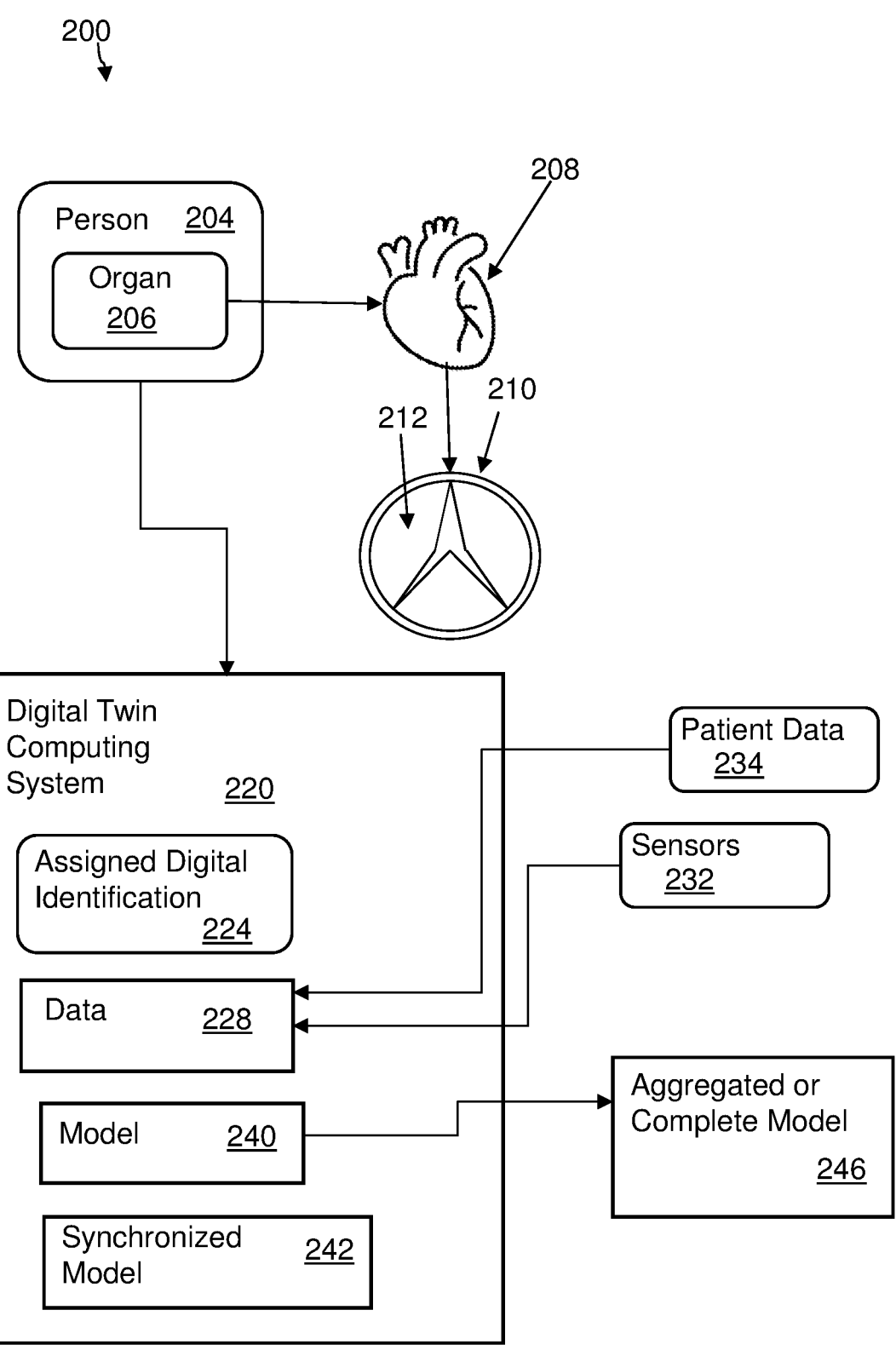
FIG. 2 is a functional schematic block diagram showing a series of operations and functional methodologies, for instructional purposes illustrating functional features of the present disclosure associated with the embodiments shown in the FIGS., which can be implemented, at least in part, in coordination with a method(s) shown in the FIGS, for generating a digital twin model or computer simulation of an organ for organ transplant or organ repairs.

Referring to FIGS. 1A, 1B, and 2, according to embodiments of the present disclosure, a computer-implemented method 100 for training a digital twin simulation for organ transplant which includes features described below. Embodiments of the present disclosure include operational actions and/or procedures. The computer-implemented method 100 includes a series of operational blocks for implementing an embodiment according to the present disclosure which can include systems shown in figures. The operational blocks of the methods and systems according to the present disclosure can include techniques, mechanism, modules, and the like for implementing the functions of the operations in accordance with the present disclosure.

Embodiments of the present disclosure include a system and method by which, a digital twin computing system can create an exact working model of the body or organ parts and can validate how the digital twin computing system can synchronize with remaining parts of the organ, and accordingly generate an appropriate digital twin model of the body or organ parts, so that bioprinting of the body part or organ can be productive and efficient.

In general, in example methods and systems, according to embodiments of the present disclosure, a digital twin simulation computing system can consider one or more portions (e.g., a heart valve of a heart) of any organ that need to be transplanted or repaired. The methods and systems include creating a complete digital twin model of the entire organ considering portions to be replaced and a retained portion of the organ. The methods and systems can identify the compatibility and synchronization of the transplant portion of the organ with a retained portion of the said organ.

While considering the compatibility and synchronization of the transplant portion, a digital twin computing system can derive the specification of the organ portion which is to be printed, so that bioprinting system can print the organ parts. The digital twin commuting system can identify the healthy portion of the organ which can be retained and can create a digital twin model of the portions of any organ which are to be replaced or repaired. Thereby, a bioprinting system can identify the specification and dimension of the organ parts which is to be printed. The digital twin computing system can consider the compatibility and synchronization of the transplant organ parts with the retained organ parts, and can predict various scenarios when there may be a failure in the synchronization. Accordingly, the methods and systems can further create post-surgery guidelines, or precautions to be followed. While creating a digital twin model of the organ parts to be transplanted, the methods and systems can consider patient's activities, surroundings, etc., and can consider factors while identifying the specification of the digital twin model.

Thereby, embodiments of the method and system of the present disclosure uses a digital twin model for creating a digital twin model of the organ parts that need to be transplanted. The method and system will consider the retaining portion of the said organ, and accordingly based on compatibility and synchronization requirements, generate an appropriate digital twin model for the organ parts which are to be transplanted.

Referring to FIGS. 1A, 1B, and 2, according to an embodiment of the present disclosure, a method 100 using a system 200 for generating a digital twin model or simulation of an organ part for an organ transplant or repair includes determining a retained portion of an organ.

The method includes gathering data, using a digital twin computing system 220 or computer, from sensors regarding the health status of the person 204 and the organ 206 to be replaced or repaired, as in block 104. For example, the organ can be a heart 208 of a person/patient 206, needing replacement of a portion 212 of a valve 210. A digital twin computing system 220 or computer can continuously gather different types of data from IoT (Internet of Things) devices or sensors connected to a person and a digital twin of the person's organs can be created. Data sources can include a CAT scan (Computed Tomography), PET scan (Positron Emission Tomography), MRI (Magnetic Resonance Imaging), or X-Ray (Energetic High-Frequency Electromagnetic Radiation) scans of a person.

Each patient can have a related digital twin, for example, hosted in a cloud digital twin library. The method includes the digital twin computing system identifying one or more organs of the person, as in block 108. In another embodiment, bone, muscle, joint and tendon data can be stored on a cloud library.

The method includes identifying one or more organs using the digital twin computing system or computer, using block 1084. As part of the identification, the computing system can assign a unique number (e.g., a machine-readable barcode), as in block 112.

Identifying an organ portion or portions of an organ, and assigning a digital identification 224, e.g., a unique number to each portion of one or more organs (e.g., including machine-readable optical label (e.g., a barcode, or matrix barcode such as a "QR CODE" ®), as in block 116. Each organ portion or part can be identified uniquely, and each portion or part can be assigned a machine readable barcode.

The method can include gathering data 228 including video or photos from one or more sensors 232. e.g., IoT feeds from a physical patient, e.g., a person, in real time, or near real time, using the digital twin computing system, as in block 120.

The method includes synchronizing 242 a digital model 240 with its physical twin counterpart to maintain an updated digital physical twin, as in block 124. The received IoT data or feed can include data from various medical testing machines or equipment such as a CAT scan.

The method includes maintaining digital twin models with defined vital parameters of each of a plurality of an organ, as in block 128. In one example, patients can register with a service proving the digital twin model.

The method includes storing digital models or digital twin models in a digital storage environment, as in block 132. Such storing can include, for example, digital storage on a remote server, or digital storage in a cloud computing environment.

The method includes updating received data 228 with patient data 234, which includes determining, for example, latest current condition of a patient, latest medications or medication updates, etc., and can also include determining latest versions of software and updating, as in block 136. The computing system can identify the medically specified condition of each organ.

The method includes identifying which portion of the organ is having a problem and will need to be replaced, as in block 140, for example, not healthy. The method identifies each portion of the organ by determining health data validation of each organ.

The computing system can identify the specification of each organ, and can validate the compatibility and synchronization of each of the parts with the entire organ. The computing system can identify which portion of the organ needs to be replaced, and will be creating a digital twin model of the organ portion needing to be transplanted, as in block 144.

The method includes the computing system simulating the digital twin model of the portion of the organ to be transplanted from the organ. The computing system can create a digital twin model of the retained portion of the organ considering current condition of the patient, as in block 148.

The method includes the computing system aggregating the individual portions, that is the retained portions and the replacement portions, for example portions for removal, for example the retained portion and to be transplant portions, into a complete or combined digital twin model, as in block 152. Accordingly, the method including creating or generating a digital twin model of the complete organ, that is, the combination of the retained portions and the replacement portions.

Once the complete digital twin model 246 of the organ is created, the computing system can simulate the complete digital twin model using the computing system, as in block 156. Based on the simulation of the complete organ, the digital twin computing system can identify how the digital twin model of the to be replaced parts are synchronizing with the retaining part(s) of the organ, as in block 160.

The method includes connecting the computing system to a knowledge corpus, as in block 164. The knowledge corpus can be created based on historical data analysis.

The method includes the computing system identifying various conditions when the complete digital twin model may fail, thereby predicting a possible organ failure or transplant success based the complete digital twin model. The method can include defining failure criteria for the organ. Based on the failure criteria, the method and system can create various guidelines or precaution to follow by the patient after an organ portion is transplanted.

The method includes identifying the compatibility and synchronization of the to be transplanted parts with retaining portions of the organ, as in block 168. Based on the compatibility, synchronizing and determining health factors of the to be transplanted portion of the digital twin computing system, and re-designing the complete digital twin model so that compatibility and synchronization with the retained portion of the organ can be increased, as in block 172.

The method includes detecting and considering the surrounding of the patient and the activities to be performed after the surgery, etc., which can accordingly be considered in the digital twin computation, represented in block 176. The method can identify what capability is required in the complete organ to perform those activities.

The method includes the computing system creating a digital twin model of the organ parts which are to be transplanted, as in block 180. Based on the digital twin model, the proposed system can identify specifications, for example, dimensions of the organ parts to be implanted or transplanted.

The method includes printing, using a 3D (dimensional) bioprinting system, one or more organ parts based on the identified specification from the digital twin model, as in block 184.

As discussed in the embodiments of the disclosure herein, a portion of a body organ can be printed with a digital twin, so that the transplanted portion can be synchronized and compatible with a remaining portion of the organ. In accordance with the present disclosure, combining a digital twin and a bioprinting can be included a method and system so that a reconstruction of the organ can be synchronized.

Figure 4:
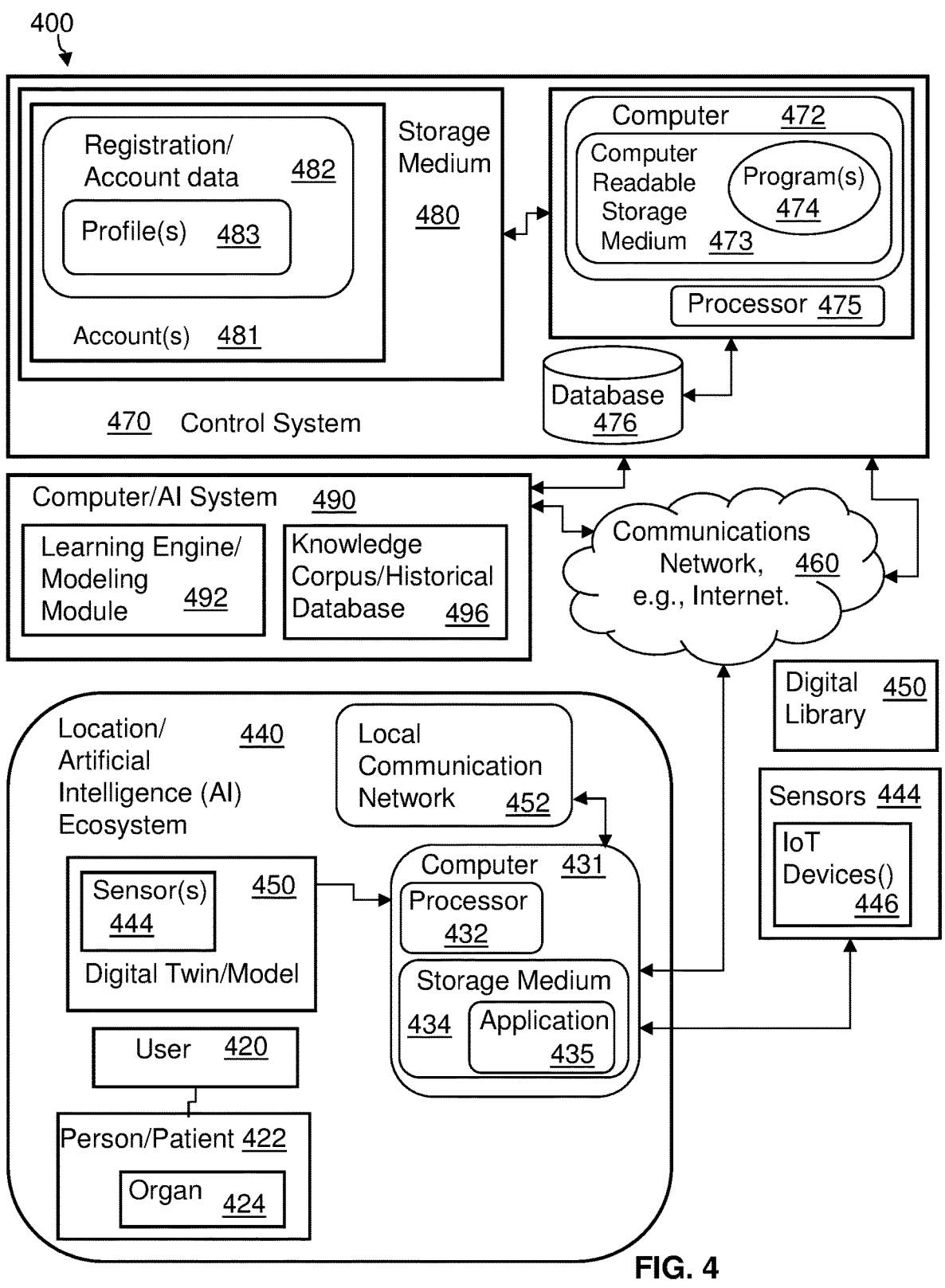
FIG. 4 is a functional schematic block diagram showing a series of operations and functional methodologies, for instructional purposes illustrating functional features of the present disclosure associated with the embodiments shown in the FIGS., which can be implemented, at least in part, in coordination with the methods shown in FIGS., for generating a digital twin model or computer simulation of an organ for organ transplant or organ repairs, according to an embodiment of the disclosure.
Figure 5:
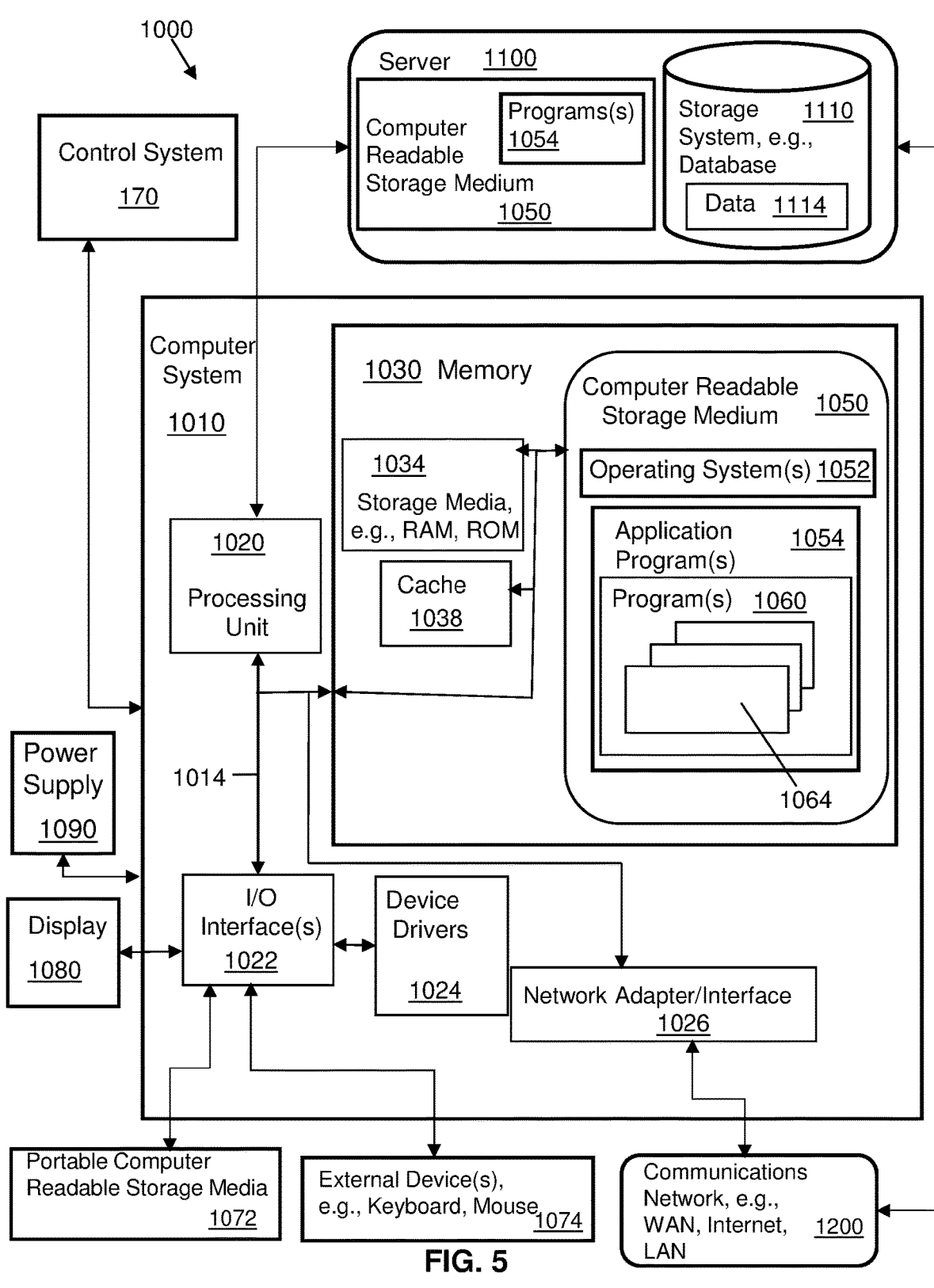
FIG. 5 is a schematic block diagram depicting a computer system according to an embodiment of the disclosure which may be incorporated, all or in part, in one or more computers or devices shown in the FIGS., and cooperates with the systems and methods shown in the FIGS.

Referring to FIGS. 3A, 4 and 5, a method 300 is computer implemented, for generating a digital twin model or computer simulation of an organ for organ transplant or organ repairs, which can be initiated by a user 420. A digital twin model or simulation of an organ part for an organ transplant or repair is generated for determining portions of an organ. The computer-implemented method includes a series of operational blocks for implementing an embodiment according to the present disclosure which can include a system shown in figures. The operational blocks of the methods and systems according to the present disclosure can include techniques, mechanism, modules, and the like for implementing the functions of the operations in accordance with the present disclosure.

Again referring to FIG. 3A, and FIG. 4, the method 300 includes receiving, at a computer, organ data of an organ 424 for a patient 422, in one example, for at least a partial organ transplant, as in block 304. The method includes identifying, using the computer, organ parts of the organ based on the organ data, the organ parts including a retained portion of the organ and a replacement portion of the organ, as in block 308. Organ data can be stored as all or part of a knowledge corpus or database 496. The method includes generating models 450, using the computer, as digital twin computer simulations of the organ parts based on the received organ data, as in block 312.

When the model is not acceptable, at block 314, the method returns to block 308. When the model is acceptable, at block 314, the method continues to block 316. The method includes determining parameters for the organ parts including dimensions of the retained portion of the organ and dimensions of the replacement portion of the organ, as in block 316.

The method includes selecting a final model of the organ parts, as in block 320. The method includes combining the final models of the organ parts into a final organ model of the organ including the replacement portion, as in block 324.

The method can include iteratively training the models based on the organ data and the parameters to generate updated models. Further, the method can include determining a best model for each of the portions of the organ.

Referring to FIG. 3B, in another embodiment according to the present disclosure, a method 350 proceeds from the method 300 shown in FIG. 4, and the method 350 includes iteratively training the models based on the organ data and the parameters to generate updated models, as in block 354. The method includes determining a best model for each of the portions of the organ, as in block 358. The method includes selecting a final model of the organ parts, as in block 362. The method includes combining the final model of the organ parts into a final organ model of the organ including the replacement portion, as in block 366. The method includes evaluating the final model to determine when the combination of the organ parts meets threshold parameters, as in block 368.

In one example, the method can further include receiving data, at the computer, from devices and sensors connected to the patient.

In one example, the method can further include receiving data, at the computer, from Internet of Things (IoT) devices 446 with respect to the patient 422, and receiving data from sensors 444 connected to the patient.

In one example, the method can include, using the computer, assigning a unique number to the model. In another example, the unique number can be a QR code.

In another example, the retained part of the organ is a healthy portion of the organ and the replacement part of the organ is an unhealthy portion of the organ.

In one example, a method can further include receiving data, at the computer, from Internet of Things (IoT) devices with respect to the patient, and receiving data from sensors connected to the patient. The method includes updating the model based on the received data from the IoT devices and the sensors to generate a near real-time simulation using the model.

The method can further include identifying, using the computer, the unhealthy portion of the organ using the updated model and other medical data received by the computer, wherein the other medical data includes medical diagnostic information and medical standards related to the organ. Determining a part of the organ for replacement can be based on the identification of the unhealthy portion of the organ. Printing, using a 3 dimensional bioprinting system, of an organ part can be based on the model.

The methods disclosed herein can further include modeling, using a computer, an organ thereby generating a model. The model can be generated using a learning engine or modeling module 192 of a computer system 190 which can be all or in part of an Artificial Intelligence (AI) system which communicates with the computer 131 and/or a control system 170. Such a computer system 190 can include or communicate with a knowledge corpus or historical database 196.

In one example, the method and operations can include determining when a model is acceptable, and the method can proceed with operations. In another example, an acceptable model can include a model meeting specified parameters. In another example, an acceptable model can be a model which has undergone several iterations. When the model is not acceptable, a method can return to a previous operation represented by a block in a flowchart.

The computer 131 can be integral to or communicating with the robotic device 148 in a device 130. A computer 190 remote from the device 148 can electronically communicate, in all or in part, with the computer 172 as part of the control system 170. The control system can include the computer

172 having a computer readable storage medium 173 which can store one or more programs 174, and a processor 175 for executing program instructions. The control system can also include a storage medium which can include registration and/or account data 182 and profiles 183 of users or entities (such entities can include robotic entities) as part of user accounts 181. User accounts 181 can be stored on a storage medium 180 which is part of the control system 170. The user accounts 181 can include registrations and account data 182 and user profiles 183. The control system can also include a computer 172 having a computer readable storage medium 173 which can store programs or code embedded on the storage medium. The program code can be executed by a processor 175. The computer 172 can communicate with a database 176. The control system 170 can also include a database 176 for storing all or part of such data as described above, and other data.

The control system can also communicate with a computer system 190 which can include a learning engine/ module 192 and a knowledge corpus or database 196. The computer system 190 can also communicate with the computer 131 of the device 130 and can be remote from the user device 130. In another example, the computer system 190 can be all or part of the control system, or all or part of the device 130. The depiction of the computer system 190 as well as the other components of the system 100 are shown as one example according to the present disclosure.

The new or different AI (Artificial Intelligence) ecosystem, or technology/communication or IT (Information Technology) ecosystem can include a local communications network 452 which can communicate with the communications network 460. The system 400 can include a learning engine/module 492, which can be at least part of the control system or communicating with the control system, for generating a model or learning model. In one example, the learning model can model workflow in a new AI or IT ecosystem for machine/devices in the new ecosystem.

In another example, the computer 431 can be part of a device. The computer can include a processor 432 and a computer readable storage medium 434 where an application 435 can be stored which can in one example, embody all or part of the method of the present disclosure. The application can include all or part of instructions to implement the method of the present disclosure, embodied in code and stored on a computer readable storage medium. The computer 431 can operate, in all or in part, in conjunction with a remote server by way of a communications network 460, for example, the Internet.

The method can include an analysis generating a model 324 based on received data. A model can also be generated by an AI system such as an output at least in part of an AI system analysis using machine learning. A model can also be generated by an AI system such as an output at least in part of an AI system analysis using machine learning.

In one example, as part of the analysis of received data including data in the knowledge corpus and historical database 196, which can be populated by historical data gathered, for example, from sensors, robotic device, or other machines or devices.

Other Embodiments and Examples

Also referring to FIG. 4, the computer 431 (e.g., a device with a computer) also can be referred to as a user device or an administrator's device, which includes the computer 431 having the processor 432 and the storage medium 434 where the application 435 can be stored. The application can embody the features of one or more methods of the present disclosure as instructions, and can be stored on the computer readable storage medium 134. The user can connect to the learning engine 492 using the compute 431. The computer 431 can further include the processor 432 for executing the application/software 435.

It is understood that the computer 431 is representative of similar computers or devices, as representative of such devices, which can include, mobile devices, smart devices, laptop computers etc.

In one example, the system of the present disclosure can include a control system 470 communicating with a computer 431 via the communications network 460. The control system can incorporate all or part of an application or software for implementing the method of the present disclosure. The control system can include a computer readable storage medium 473 where account data and/or registration data 482 can be stored. User profiles 483 can be part of the account data and stored on the storage medium 480. The control system can include a computer 472 having computer readable storage medium 473 and software programs 474 stored therein. A processor 475 can be used to execute or implement the instructions of the software program. The control system can also include a database 476.

In another example and embodiment, profiles can be saved for entities such as users, participants, operators, human operators, or robotic devices. Such profiles can supply data regarding the user and history of deliveries for analysis. In one example, a user can register or create an account using the control system 470 which can include one or more profiles 483 as part of registration and/or account data 482. The registration can include profiles for each user having personalized data. For example, users can register using a website via their computer and GUI (Graphical User Interface) interface. The registration or account data 482 can include profiles 483 for an account 481 for each user. Such accounts can be stored on the control system 470, which can also use the database 476 for data storage. A user and a related account can refer to, for example, a person, or an entity, or a corporate entity, or a corporate department, or another machine such as an entity for automation such as a system using, in all or in part, artificial intelligence.

Methods and systems according to the present disclosure is discussed with reference to FIG. 4, which is a functional system or diagram 400 and includes components and operations for embodiments according to the present disclosure, and is used herein for reference when describing the operational steps of the methods and systems of the present disclosure. Additionally, the functional system 400, according to an embodiment of the present disclosure, depicts functional operations indicative of the embodiments discussed herein. Such functional diagrams may have similar components and may have the same or different reference numerals for elements as examples.

More Examples and Embodiments

Operational blocks and system components shown in one or more of the figures may be similar to operational blocks and system components in other figures. The diversity of operational blocks and system components depict example embodiments and aspects according to the present disclosure. For example, methods and systems shown are intended as example embodiments which can include aspects/operations shown and discussed previously in the present disclosure, and in one example, continuing from a previous method shown in another flow chart.

Additional Examples and Embodiments

In the embodiment of the present disclosure shown in FIGS. 1 and 2, a computer can be part of a remote computer or a remote server, for example, remote server 1100 (FIG. 5). In another embodiment, a computer can be part of a mobile device and provide execution of the functions of the present disclosure. In still another embodiment, parts of the execution of functions of the present disclosure can be shared between the control system computer and the mobile device computer, for example, the control system function as a back end of a program or programs embodying the present disclosure and the mobile device computer functioning as a front end of the program or programs.

The computer can be part of the mobile device, or a remote computer communicating with the mobile device. In another example, a mobile device and a remote computer can work in combination to implement the method of the present disclosure using stored program code or instructions to execute the features of the method(s) described herein. Such interactions and mechanisms are described in further detail herein and referred to regarding components of a computer system, such as computer readable storage media, which are shown in one embodiment in FIG. 5 and described in more detail in regards thereto referring to one or more computer systems 1010. Features shown herein in the figures, can include and other similar components and features are also in an embodiment of a computer system shown in FIG. 5 referring to a computer system 1010, which may include one or more computer components.

The method according to the present disclosure, can include a computer for implementing the features of the method, according to the present disclosure, as part of a control system. In another example, a computer as part of a control system can work in corporation with a mobile device computer in concert with communication system for implementing the features of the method according to the present disclosure. In another example, a computer for implementing the features of the method can be part of a mobile device and thus implement the method locally.

Specifically, regarding the control system 470, shown in FIG. 4, the computer 431, or in one example, devices which can belong to one or more users, can be in communication with the control system 470 via the communications network 460. In the embodiment of the control system shown in FIG. 4, the control system 470 includes a computer 472 communicating with a database 476 and one or more programs 474 stored on a computer readable storage medium 473. In the embodiment of the disclosure shown in FIG. 4, the computer communicates with the control system 470 and the one or more programs 474 stored on a computer readable storage medium 473. The control system includes the computer 472 having a processor 475, which also has access to the database 476.

The control system 470 can include a storage medium 480 for maintaining a registration 482 of users and their devices for analysis of the audio input. Such registration can include user profiles 483, which can include user data supplied by the users in reference to registering and setting-up an account. In an embodiment, the method and system which incorporates the present disclosure includes the control system (generally referred to as the back-end) in combination and cooperation with a front end of the method and system, which can be the application 435. In one example, the application 435 is stored on a device, for example, a computer or device on location, and can access data and additional programs at a back end of the application, e.g., control system 470.

The control system can also be part of a software application implementation, and/or represent a software application having a front-end user part and a back-end part providing functionality. In an embodiment, the method and system which incorporates the present disclosure includes the control system (which can be generally referred to as the back-end of the software application which incorporates a part of the method and system of an embodiment of the present application) in combination and cooperation with a front end of the software application incorporating another part of the method and system of the present application at the device, as in the example shown in FIG. 4 of the computer 431 having the application 435. The application 435 is stored on the device or computer and can access data and additional programs at the back end of the application, for example, in the program(s) 474 stored in the control system 470.

The program(s) 474 can include, all or in part, a series of executable steps for implementing the method of the present disclosure. A program, incorporating the present method, can be all or in part stored in the computer readable storage medium on the control system or, in all or in part, on a computer or device. It is envisioned that the control system 470 can not only store the profile of users, but in one embodiment, can interact with a website for viewing on a display of a device such as a mobile device, or in another example the Internet, and receive user input related to the method and system of the present disclosure. It is understood that FIG. 4 depicts one or more profiles 483, however, the method can include multiple profiles, users, registrations, etc. It is envisioned that a plurality of users or a group of users can register and provide profiles using the control system for use according to the method and system of the present disclosure.

Still Further Embodiments and Examples

It is understood that the features shown in some of the FIGS., for example block diagrams, are functional representations of features of the present disclosure. Such features are shown in embodiments of the systems and methods of the present disclosure for illustrative purposes to clarify the functionality of features of the present disclosure.

The methods and systems of the present disclosure can include a series of operation blocks for implementing one or more embodiments according to the present disclosure. In some examples, operational blocks of one or more FIGS. may be similar to operational blocks shown in another figure. A method shown in one FIG. may be another example embodiment which can include aspects/operations shown in another FIG. and discussed previously.

Additional Embodiments and Examples

Account data, for instance, including profile data related to a user, and any data, personal or otherwise, can be collected and stored, for example, in the control system 170. It is understood that such data collection is done with the knowledge and consent of a user, and stored to preserve privacy, which is discussed in more detail below. Such data can include personal data, and data regarding personal items. In one example a user can register 482 have an account 481 with a user profile 483 on a control system 470, which is discussed in more detail below. For example, data can be collected using techniques as discussed above, for example, using cameras, and data can be uploaded to a user profile by the user. A user can include, for example, a corporate entity, or department of a business, or a homeowner, or any end user, a human operator, or a robotic device, or other personnel of a business.

Regarding collection of data with respect to the present disclosure, such uploading or generation of profiles is voluntary by the one or more users, and thus initiated by and with the approval of a user. Thereby, a user can opt-in to establishing an account having a profile according to the present disclosure. Similarly, data received by the system or inputted or received as an input is voluntary by one or more users, and thus initiated by and with the approval of the user. Thereby, a user can opt-in to input data according to the present disclosure. Such user approval also includes a user's option to cancel such profile or account, and/or input of data, and thus opt-out, at the user's discretion, of capturing communications and data. Further, any data stored or collected is understood to be intended to be securely stored and unavailable without authorization by the user, and not available to the public and/or unauthorized users. Such stored data is understood to be deleted at the request of the user and deleted in a secure manner. Also, any use of such stored data is understood to be, according to the present disclosure, only with the user's authorization and consent.

In one or more embodiments of the present invention, a user(s) can opt-in or register with a control system, voluntarily providing data and/or information in the process, with the user's consent and authorization, where the data is stored and used in the one or more methods of the present disclosure. Also, a user(s) can register one or more user electronic devices for use with the one or more methods and systems according to the present disclosure. As part of a registration, a user can also identify and authorize access to one or more activities or other systems (e.g., audio and/or video systems). Such opt-in of registration and authorizing collection and/or storage of data is voluntary and a user may request deletion of data (including a profile and/or profile data), un-registering, and/or opt-out of any registration. It is understood that such opting-out includes disposal of all data in a secure manner. A user interface can also allow a user or an individual to remove all their historical data.

Other Additional Embodiments and Examples

In one example, Artificial Intelligence (AI) can be used, all or in part, for generating a model or a learning model as discussed herein in embodiments of the present disclosure. An Artificial Intelligence (AI) System can include machines, computer, and computer programs which are designed to be intelligent or mirror intelligence. Such systems can include computers executing algorithms. AI can include machine learning and deep learning. For example, deep learning can include neural networks. An AI system can be cloud based, that is, using a cloud-based computing environment having computing resources.

In another example, the control system 470 can be all or part of an Artificial Intelligence (AI) system. For example, the control system can be one or more components of an AI system.

It is also understood that one or more methods according to embodiments of the present disclosure, can be incorporated into (Artificial Intelligence) AI devices, components or be part of an AI system, which can communicate with respective AI systems and components, and respective AI system platforms. Thereby, such programs or an application incorporating the method of the present disclosure, as discussed above, can be part of an AI system. In one embodiment according to the present invention, it is envisioned that the control system can communicate with an AI system, or in another example can be part of an AI system. The control system can also represent a software application having a front-end user part and a back-end part providing functionality, which can in one or more examples, interact with, encompass, or be part of larger systems, such as an AI system. In one example, an AI device can be associated with an AI system, which can be all or in part, a control system and/or a content delivery system, and be remote from an AI device. Such an AI system can be represented by one or more servers storing programs on computer readable medium which can communicate with one or more AI devices. The AI system can communicate with the control system, and in one or more embodiments, the control system can be all or part of the AI system or vice versa.

It is understood that as discussed herein, a download or downloadable data can be initiated using a voice command or using a mouse, touch screen, etc. In such examples a mobile device can be user initiated, or an AI device can be used with consent and permission of users. Other examples of AI devices include devices which include a microphone, speaker, and can access a cellular network or mobile network, a communications network, or the Internet, for example, a vehicle having a computer and having cellular or satellite communications, or in another example, IoT (Internet of Things) devices, such as appliances, having cellular network or Internet access.

Further Discussion Regarding Examples and Embodiments

It is understood that a set or group is a collection of distinct objects or elements. The objects or elements that make up a set or group can be anything, for example, numbers, letters of the alphabet, other sets, a number of people or users, and so on. It is further understood that a set or group can be one element, for example, one thing or a number, in other words, a set of one element, for example, one or more users or people or participants.

The descriptions of the various embodiments of the present invention have been presented for purposes of illustration, but are not intended to be exhaustive or limited to the embodiments disclosed. Likewise, examples of features or functionality of the embodiments of the disclosure described herein, whether used in the description of a particular embodiment, or listed as examples, are not intended to limit the embodiments of the disclosure described herein, or limit the disclosure to the examples described herein. Such examples are intended to be examples or exemplary, and non-exhaustive. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further Additional Examples and Embodiments

Referring to FIG. 5, an embodiment of system or computer environment 1000, according to the present disclosure, includes a computer system 1010 shown in the form of a generic computing device. The method 100, for example, may be embodied in a program 1060, including program instructions, embodied on a computer readable storage device, or a computer readable storage medium, for example, generally referred to as computer memory 1030 and more specifically, computer readable storage medium 1050. Such memory and/or computer readable storage media includes non-volatile memory or non-volatile storage, also known and referred to non-transient computer readable storage media, or non-transitory computer readable storage media. For example, such non-volatile memory can also be disk storage devices, including one or more hard drives. For example, memory 1030 can include storage media 1034 such as RAM (Random Access Memory) or ROM (Read Only Memory), and cache memory 1038. The program 1060 is executable by the processor 1020 of the computer system 1010 (to execute program steps, code, or program code). Additional data storage may also be embodied as a database 1110 which includes data 1114. The computer system 1010 and the program 1060 are generic representations of a computer and program that may be local to a user, or provided as a remote service (for example, as a cloud based service), and may be provided in further examples, using a website accessible using the communications network 1200 (e.g., interacting with a network, the Internet, or cloud services). It is understood that the computer system 1010 also generically represents herein a computer device or a computer included in a device, such as a laptop or desktop computer, etc., or one or more servers, alone or as part of a datacenter. The computer system can include a network adapter/interface 1026, and an input/output (I/O) interface(s) 1022. The I/O interface 1022 allows for input and output of data with an external device 1074 that may be connected to the computer system. The network adapter/interface 1026 may provide communications between the computer system a network generically shown as the communications network 1200.

The computer 1010 may be described in the general context of computer system-executable instructions, such as program modules, being executed by a computer system. Generally, program modules may include routines, programs, objects, components, logic, data structures, and so on that perform particular tasks or implement particular abstract data types. The method steps and system components and techniques may be embodied in modules of the program 1060 for performing the tasks of each of the steps of the method and system. The modules are generically represented in the figure as program modules 1064. The program 1060 and program modules 1064 can execute specific steps, routines, sub-routines, instructions or code, of the program.

The method of the present disclosure can be run locally on a device such as a mobile device, or can be run a service, for instance, on the server 1100 which may be remote and can be accessed using the communications network 1200. The program or executable instructions may also be offered as a service by a provider. The computer 1010 may be practiced in a distributed cloud computing environment where tasks are performed by remote processing devices that are linked through a communications network 1200. In a distributed cloud computing environment, program modules may be located in both local and remote computer system storage media including memory storage devices.

More specifically, the system or computer environment 1000 includes the computer system 1010 shown in the form of a general-purpose computing device with illustrative periphery devices. The components of the computer system 1010 may include, but are not limited to, one or more processors or processing units 1020, a system memory 1030, and a bus 1014 that couples various system components including system memory 1030 to processor 1020.

The bus 1014 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer 1010 can include a variety of computer readable media. Such media may be any available media that is accessible by the computer 1010 (e.g., computer system, or server), and can include both volatile and non-volatile media, as well as removable and non-removable media. Computer memory 1030 can include additional computer readable media in the form of volatile memory, such as random access memory (RAM) 1034, and/or cache memory 1038. The computer 1010 may further include other removable/non-removable, volatile/non-volatile computer storage media, in one example, portable computer readable storage media 1072. In one embodiment, the computer readable storage medium 1050 can be provided for reading from and writing to a non-removable, non-volatile magnetic media. The computer readable storage medium 1050 can be embodied, for example, as a hard drive. Additional memory and data storage can be provided, for example, as the storage system 1110 (e.g., a database) for storing data 1114 and communicating with the processing unit 1020. The database can be stored on or be part of a server 1100. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1014 by one or more data media interfaces. As will be further depicted and described below, memory 1030 may include at least one program product which can include one or more program modules that are configured to carry out the functions of embodiments of the present invention.

The method(s) described in the present disclosure, for example, may be embodied in one or more computer programs, generically referred to as a program 1060 and can be stored in memory 1030 in the computer readable storage medium 1050. The program 1060 can include program modules 1064. The program modules 1064 can generally carry out functions and/or methodologies of embodiments of the invention as described herein. The one or more programs 1060 are stored in memory 1030 and are executable by the processing unit 1020. By way of example, the memory 1030 may store an operating system 1052, one or more application programs 1054, other program modules, and program data on the computer readable storage medium 1050. It is understood that the program 1060, and the operating system 1052 and the application program(s) 1054 stored on the computer readable storage medium 1050 are similarly executable by the processing unit 1020. It is also understood that the application 1054 and program(s) 1060 are shown generically, and can include all of, or be part of, one or more applications and program discussed in the present disclosure, or vice versa, that is, the application 1054 and program 1060 can be all or part of one or more applications or programs which are discussed in the present disclosure. It is also understood that a control system 470, communicating with a computer system, can include all or part of the computer system 1010 and its components, and/or the control system can communicate with all or part of the computer system 1010 and its components as a remote computer system, to achieve the control system functions described in the present disclosure. The control system function, for example, can include storing, processing, and executing software instructions to perform the functions of the present disclosure. It is also understood that the one or more computers or computer systems can include all or part of the computer system 1010 and its components, and/or the one or more computers can communicate with all or part of the computer system 1010 and its components as a remote computer system, to achieve the computer functions described in the present disclosure.

In an embodiment according to the present disclosure, one or more programs can be stored in one or more computer readable storage media such that a program is embodied and/or encoded in a computer readable storage medium. In one example, the stored program can include program instructions for execution by a processor, or a computer system having a processor, to perform a method or cause the computer system to perform one or more functions. For example, in one embedment according to the present disclosure, a program embodying a method is embodied in, or encoded in, a computer readable storage medium, which includes and is defined as, a non-transient or non-transitory computer readable storage medium. Thus, embodiments or examples according to the present disclosure, of a computer readable storage medium do not include a signal, and embodiments can include one or more non-transient or non-transitory computer readable storage mediums. Thereby, in one example, a program can be recorded on a computer readable storage medium and become structurally and functionally interrelated to the medium.

The computer 1010 may also communicate with one or more external devices 1074 such as a keyboard, a pointing device, a display 1080, etc.; one or more devices that enable a user to interact with the computer 1010; and/or any devices (e.g., network card, modem, etc.) that enables the computer 1010 to communicate with one or more other computing devices. Such communication can occur via the Input/Output (I/O) interfaces 1022. A power supply 1090 can also connect to the computer using an electrical power supply interface (not shown). Still yet, the computer 1010 can communicate with one or more networks 1200 such as a local area network (LAN), a general wide area network (WAN), and/or a public network (e.g., the Internet) via network adapter/interface 1026. As depicted, network adapter 1026 communicates with the other components of the computer 1010 via bus 1014. It should be understood that although not shown, other hardware and/or software components could be used in conjunction with the computer 1010. Examples, include, but are not limited to: microcode, device drivers 1024, redundant processing units, external disk drive arrays, RAID systems, tape drives, and data archival storage systems, etc.

It is understood that a computer or a program running on the computer 1010 may communicate with a server, embodied as the server 1100, via one or more communications networks, embodied as the communications network 1200. The communications network 1200 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

In one example, a computer can use a network which may access a website on the Web (World Wide Web) using the Internet. In one embodiment, a computer 1010, including a mobile device, can use a communications system or network 1200 which can include the Internet, or a public switched telephone network (PSTN) for example, a cellular network. The PSTN may include telephone lines, fiber optic cables, microwave transmission links, cellular networks, and communications satellites. The Internet may facilitate numerous searching and texting techniques, for example, using a cell phone or laptop computer to send queries to search engines via text messages (SMS), Multimedia Messaging Service (MMS) (related to SMS), email, or a web browser. The search engine can retrieve search results, that is, links to websites, documents, or other downloadable data that correspond to the query, and similarly, provide the search results to the user via the device as, for example, a web page of search results.

Still Further Additional Examples and Embodiments

Figure 6:
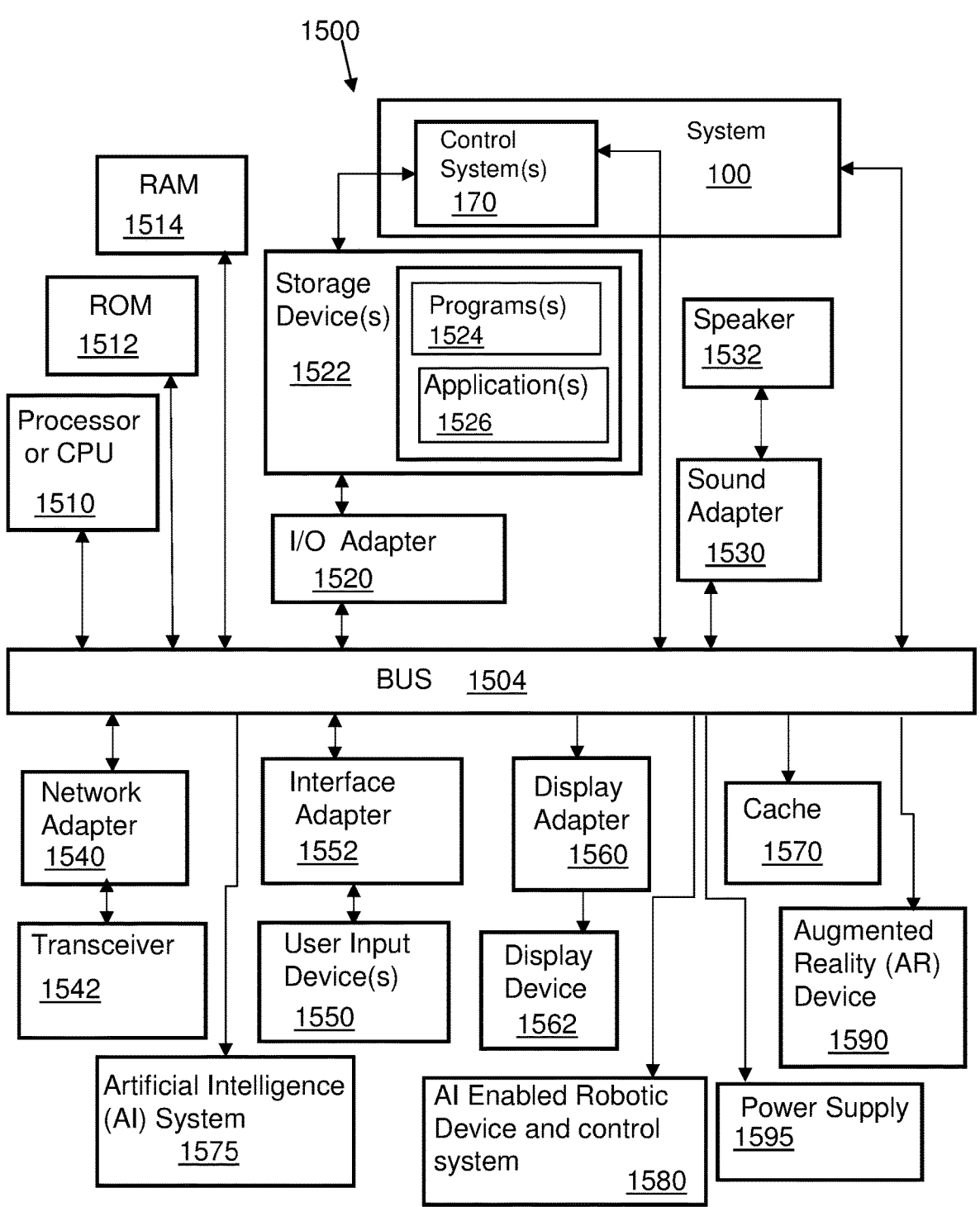
FIG. 6 is a schematic block diagram of a system depicting system components interconnected using a bus. The components for use, in all or in part, with the embodiments of the present disclosure, in accordance with one or more embodiments of the present disclosure.

Referring to FIG. 6, an example system 1500 for use with the embodiments of the present disclosure is depicted. The system 1500 includes a plurality of components and elements connected via a system bus 1504. At least one processor (CPU) 1510, is connected to other components via the system bus 1504. A cache 1570, a Read Only Memory (ROM) 1512, a Random Access Memory (RAM) 1514, an input/output (I/O) adapter 1520, a sound adapter 1530, a network adapter 1540, a user interface adapter 1552, a display adapter 1560 and a display device 1562, are also operatively coupled to the system bus 1504 of the system 1500. An AR device 1580 can also be operatively coupled to the bus 1504. An AI enabled robotic device and control system 1580 can also be operatively coupled to the bus 1504. Such a robot and control system 1580 can incorporate all or part of embodiments of the present disclosure and discussed hereinbefore. An artificial intelligence (AI) system 1575 or an AI ecosystem can also be operatively coupled to the bus 1504. A power supply 1595 can also be operatively connected to the bus 1504 for providing power to components and for functions according to the present disclosure. An augmented reality (AR) device 1590 can also be operatively connected to the bus 1504 for providing augmented reality output to a wearable augmented reality device, such as AR glasses or an AR headset.

One or more storage devices 1522 are operatively coupled to the system bus 1504 by the I/O adapter 1520. The storage device 1522, for example, can be any of a disk storage device (e.g., a magnetic or optical disk storage device), a solid state magnetic device, and so forth. The storage device 1522 can be the same type of storage device or different types of storage devices. The storage device can include, for example, but not limited to, a hard drive or flash memory and be used to store one or more programs 1524 or applications 1526. The programs and applications are shown as generic components and are executable using the processor 1510. The program 1524 and/or application 1526 can include all of, or part of, programs or applications discussed in the present disclosure, as well vice versa, that is, the program 1524 and the application 1526 can be part of other applications or program discussed in the present disclosure.

The system 1500 can include the control system 170 which is part of the system 100 (described in further detail hereinbefore) and can communicate with the system bus independently or as part of the system 100, and thus can communicate with the other components of the system 1500 via the system bus. In one example, the storage device 1522, via the system bus, can communicate with the control system 170 which has various functions as described in the present disclosure.

In one aspect, a speaker 1532 is operatively coupled to system bus 1504 by the sound adapter 1530. A transceiver 1542 is operatively coupled to system bus 1504 by the network adapter 1540. A display 1562 is operatively coupled to the system bus 1504 by the display adapter 1560.

In another aspect, one or more user input devices 1550 are operatively coupled to the system bus 1504 by the user interface adapter 1552. The user input devices 1550 can be, for example, any of a keyboard, a mouse, a keypad, an image capture device, a motion sensing device, a microphone, a device incorporating the functionality of at least two of the preceding devices, and so forth. Other types of input devices can also be used, while maintaining the spirit of the present invention. The user input devices 1550 can be the same type of user input device or different types of user input devices. The user input devices 1550 are used to input and output information to and from the system 1500.

Other Aspects and Examples

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures of the present disclosure illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Additional Aspects and Examples

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 7:
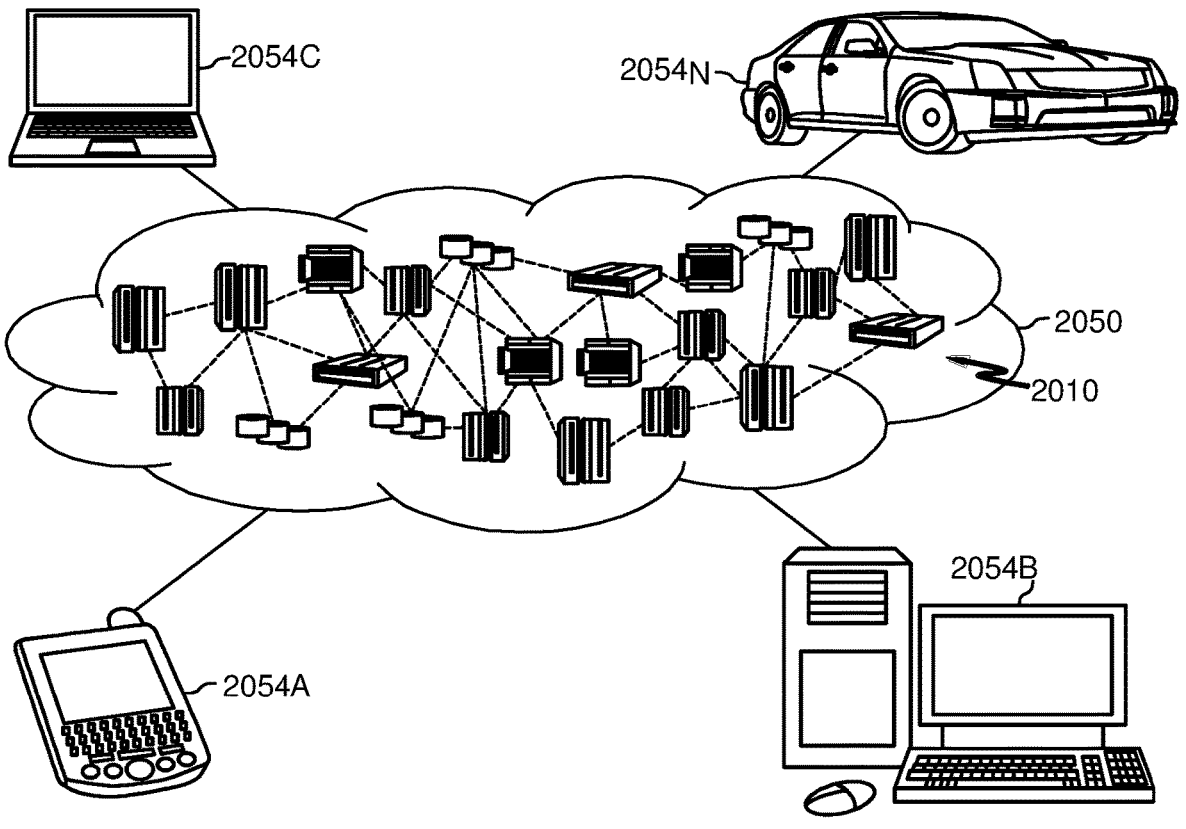
FIG. 7 is a block diagram depicting a cloud computing environment according to an embodiment of the present invention.

Referring now to FIG. 7, illustrative cloud computing environment 2050 is depicted. As shown, cloud computing environment 2050 includes one or more cloud computing nodes 2010 with which local computing devices used by cloud consumers, such as, for example, personal digital assistant (PDA) or cellular telephone 2054A, desktop computer 2054B, laptop computer 2054C, and/or automobile computer system 2054N may communicate. Nodes 2010 may communicate with one another. They may be grouped (not shown) physically or virtually, in one or more networks, such as Private, Community, Public, or Hybrid clouds as described hereinabove, or a combination thereof. This allows cloud computing environment 2050 to offer infrastructure, platforms and/or software as services for which a cloud consumer does not need to maintain resources on a local computing device. It is understood that the types of computing devices 2054A-N shown in FIG. 7 are intended to be illustrative only and that computing nodes 2010 and cloud computing environment 2050 can communicate with any type of computerized device over any type of network and/or network addressable connection (e.g., using a web browser).

Figure 8:
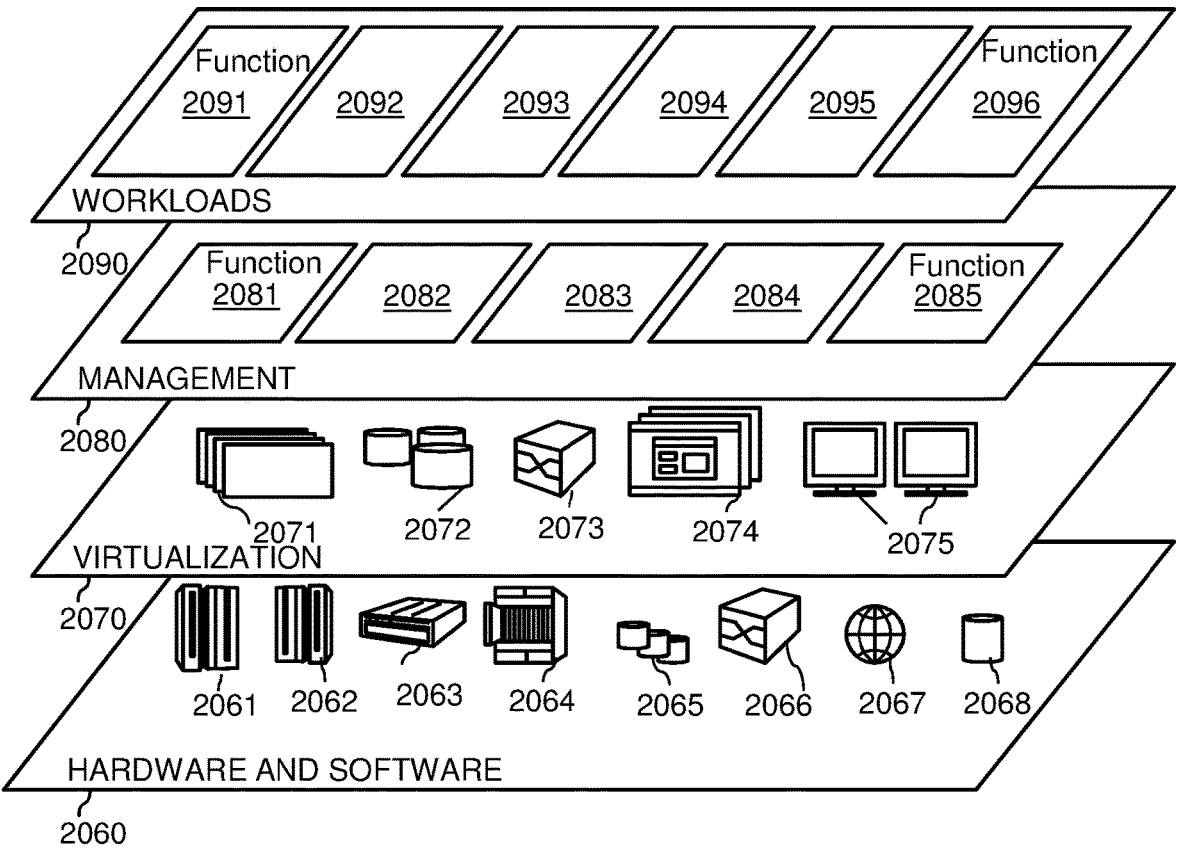
FIG. 8 is a block diagram depicting abstraction model layers according to an embodiment of the present invention.

Referring now to FIG. 8, a set of functional abstraction layers provided by cloud computing environment 2050 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 2060 includes hardware and software components. Examples of hardware components include: mainframes 2061; RISC (Reduced Instruction Set Computer) architecture based servers 2062; servers 2063; blade servers 2064; storage devices 2065; and networks and networking components 2066. In some embodiments, software components include network application server software 2067 and database software 2068.

Virtualization layer 2070 provides an abstraction layer from which the following examples of virtual entities may be provided: virtual servers 2071; virtual storage 2072; virtual networks 2073, including virtual private networks; virtual applications and operating systems 2074; and virtual clients 2075.

In one example, management layer 2080 may provide the functions described below. Resource provisioning 2081 provides dynamic procurement of computing resources and other resources that are utilized to perform tasks within the cloud computing environment. Metering and Pricing 2082 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 2083 provides access to the cloud computing environment for consumers and system administrators. Service level management 2084 provides cloud computing resource allocation and management such that required service levels are met. Service Level Agreement (SLA) planning and fulfillment 2085 provide pre-arrangement for, and procurement of, cloud computing resources for which a future requirement is anticipated in accordance with an SLA.

Workloads layer 2090 provides examples of functionality for which the cloud computing environment may be utilized.

Examples of workloads and functions which may be provided from this layer include: mapping and navigation 2091; software development and lifecycle management 2092; virtual classroom education delivery 2093; data analytics processing 2094; transaction processing 2095; and generating a digital model or computer simulation 2096, for example, a digital twin model of a patient's body organ.

What is claimed is:

1. A computer-implemented method for generating a digital twin model or computer simulation of an organ for organ transplant or organ repairs, comprising:

receiving, at a computer, organ data of an organ for a patient, the organ data describing both healthy tissue and diseased tissue of the organ of the patient;

identifying, using the computer, organ parts of the organ based on the organ data, the organ parts including a retained portion of the organ and a replacement portion of the organ, wherein the retained portion of the organ is a healthy portion of the organ having the healthy tissue and the replacement portion of the organ is an unhealthy portion of the organ having the diseased tissue;

generating models, using the computer, as digital twin computer simulations of the organ parts based on the received organ data and the identification of the organ parts, the models including a first digital twin simulation of the replacement portion of the organ and a second digital twin simulation of the retained portion of the organ;

the generating of the models includes determining parameters for the organ parts, the parameters including dimensions of the retained portion of the organ and dimensions of the replacement portion of the organ; and aggregating, using the computer, the retained portion and the replacement portion, into a combined digital twin model of the organ.

2. The method of claim 1, further comprising:

selecting a final model for each of the organ parts; and combining the final models of the organ parts into a final organ model of the organ including the replacement portion.

3. The method of claim 1, further comprising:

iteratively training the models based on the organ data and the parameters to generate updated models; and determining a best model for each of the portions of the organ.

4. The method of claim 1, further comprising:

iteratively training the models based on the organ data and the parameters to generate updated models;

determining a best model for each of the portions of the organ;

selecting a final model of the organ parts;

combining the final model of the organ parts into a final organ model of the organ including the replacement portion; and evaluating the final model to determine when the combination of the organ parts meets threshold parameters.

5. The method of claim 1, further comprising:

receiving data, at the computer, from devices and sensors connected to the patient.

6. The method of claim 1, further comprising:

receiving data, at the computer, from Internet of Things (IoT) devices with respect to the patient, and receiving data from sensors connected to the patient.

7. The method of claim 1, further comprising:

assigning, using the computer, a unique number to the model, wherein the unique number is a barcode.

8. The method of claim 1, further comprising:

receiving data, at the computer, from Internet of Things (IoT) devices with respect to the patient, and receiving data from sensors connected to the patient; and updating the models based on the received data from the IoT devices and the sensors to generate a near real time simulation using the updated models.

9. The method of claim 8, further comprising:

identifying, using the computer, the unhealthy portion of the organ using the updated models and other medical data received by the computer, wherein the other medical data includes medical diagnostic information and medical standards related to the organ.

10. The method of claim 9, further comprising:

determining a part of the organ for replacement based on the identification of the unhealthy portion of the organ.

11. The method of claim 1, further comprising:

printing, using a 3-dimensional bioprinting system, an organ part based on the model.

12. A computer program product for generating a digital twin model or computer simulation of an organ for organ transplant or organ repairs, the computer program product comprising a computer readable storage medium having program instructions embodied therewith, the program instructions executable by a computer to cause the computer to perform functions, by the computer, comprising the functions to:

receive, at a computer, organ data of an organ for a patient, the organ data describing both healthy tissue and diseased tissue of the organ of the patient;

identify, using the computer, organ parts of the organ based on the organ data, the organ parts including a retained portion of the organ and a replacement portion of the organ, wherein the retained portion of the organ is a healthy portion of the organ having the healthy tissue and the replacement portion of the organ is an unhealthy portion of the organ having the diseased tissue;

generate models, using the computer, as digital twin computer simulations of the organ parts based on the received organ data and the identification of the organ parts, the models including a first digital twin simulation of the replacement portion of the organ and a second digital twin simulation of the retained portion of the organ;

the generation of the models includes determine parameters for the organ parts, the parameters including dimensions of the retained portion of the organ and dimensions of the replacement portion of the organ; and aggregate, using the computer, the retained portion and the replacement portion, into a combined digital twin model of the organ.

* * * * *